US010449385B2

(12) United States Patent
Ju et al.

(10) Patent No.: US 10,449,385 B2
(45) Date of Patent: Oct. 22, 2019

(54) RADIATION THERAPY DEVICE AND QUALITY CONTROL METHOD FOR RADIATION THERAPY DEVICE

(71) Applicant: Samsung Life Public Welfare Foundation, Seoul (KR)

(72) Inventors: Sang Gyu Ju, Seoul (KR); Chae Seon Hong, Gyeonggi-do (KR); Doo Ho Chol, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 402 days.

(21) Appl. No.: 15/315,093

(22) PCT Filed: Jul. 17, 2015

(86) PCT No.: PCT/KR2015/007456
§ 371 (c)(1),
(2) Date: Nov. 30, 2016

(87) PCT Pub. No.: WO2016/010398
PCT Pub. Date: Jan. 21, 2016

(65) Prior Publication Data
US 2017/0197091 A1    Jul. 13, 2017

(30) Foreign Application Priority Data

Jul. 18, 2014 (KR) .................. 10-2014-0091325

(51) Int. Cl.
*A61N 5/10* (2006.01)
(52) U.S. Cl.
CPC ............. *A61N 5/10* (2013.01); *A61N 5/1048* (2013.01); *A61N 5/1049* (2013.01);
(Continued)

(58) Field of Classification Search
CPC ...... A61N 5/10; A61N 5/1048; A61N 5/1049; A61N 5/1064; A61N 5/1065; A61N 5/1075; A61N 2005/1054; A61N 2005/1076
See application file for complete search history.

(56) References Cited

U.S. PATENT DOCUMENTS 6,260,999 B1   7/2001 Wofford et al.
6,322,249 B1 * 11/2001 Wofford ............... A61N 5/1049
                                                      378/152
(Continued)

FOREIGN PATENT DOCUMENTS

DE    100 36 444 A1    2/2001
JP    2002-272862 A    9/2002
(Continued)

OTHER PUBLICATIONS

International Search Report and Written Opinion issued by Korean Patent Office, acting as the International Searching Authority, for International Application PCT/KR2015/007456 dated Oct. 13, 2015.

*Primary Examiner* — Thomas R Artman
(74) *Attorney, Agent, or Firm* — McCarter & English, LLP

(57) ABSTRACT

An embodiment of the present invention provides a radiation therapy device including: a main body; a gantry coupled to a side of the main part and rotatable relative to the main part in at least one direction; a radiation head provided on a side of the gantry to emit radiation; an image acquisition unit facing the radiation head to detect radiation emitted from the radiation head and obtain images by converting the detected radiation into electric signals; and a reference image acquisition frame provided on a side of the radiation head and including a plurality of markers formed thereon.

8 Claims, 5 Drawing Sheets

(52) U.S. Cl.
CPC ......... *A61N 5/1064* (2013.01); *A61N 5/1075* (2013.01); *A61N 2005/1054* (2013.01); *A61N 2005/1076* (2013.01)

(56) References Cited

U.S. PATENT DOCUMENTS

| | | |
|---|---|---|
| 7,345,274 B2 | 3/2008 | Nilsson |
| 8,418,288 B2 | 4/2013 | Miller et al. |
| 9,199,093 B2 | 12/2015 | Brusasco et al. |
| 10,019,789 B2 | 7/2018 | Han et al. |
| 2011/0103556 A1 | 5/2011 | Carn |
| 2015/0343240 A1* | 12/2015 | Beaumont ............ A61N 5/1075 378/207 |
| 2016/0151644 A1 | 6/2016 | Cheng et al. |
| 2016/0225132 A1 | 8/2016 | Han et al. |

FOREIGN PATENT DOCUMENTS

| | | |
|---|---|---|
| JP | 2005-524449 A | 8/2005 |
| JP | 2011-519643 A | 7/2011 |
| KR | 10-1007367 B1 | 1/2011 |
| KR | 10-2012-0097855 A | 9/2012 |
| KR | 10-1249815 B1 | 4/2013 |
| KR | 10-1341288 B1 | 12/2013 |
| WO | WO 2005/018734 A2 | 3/2005 |

\* cited by examiner

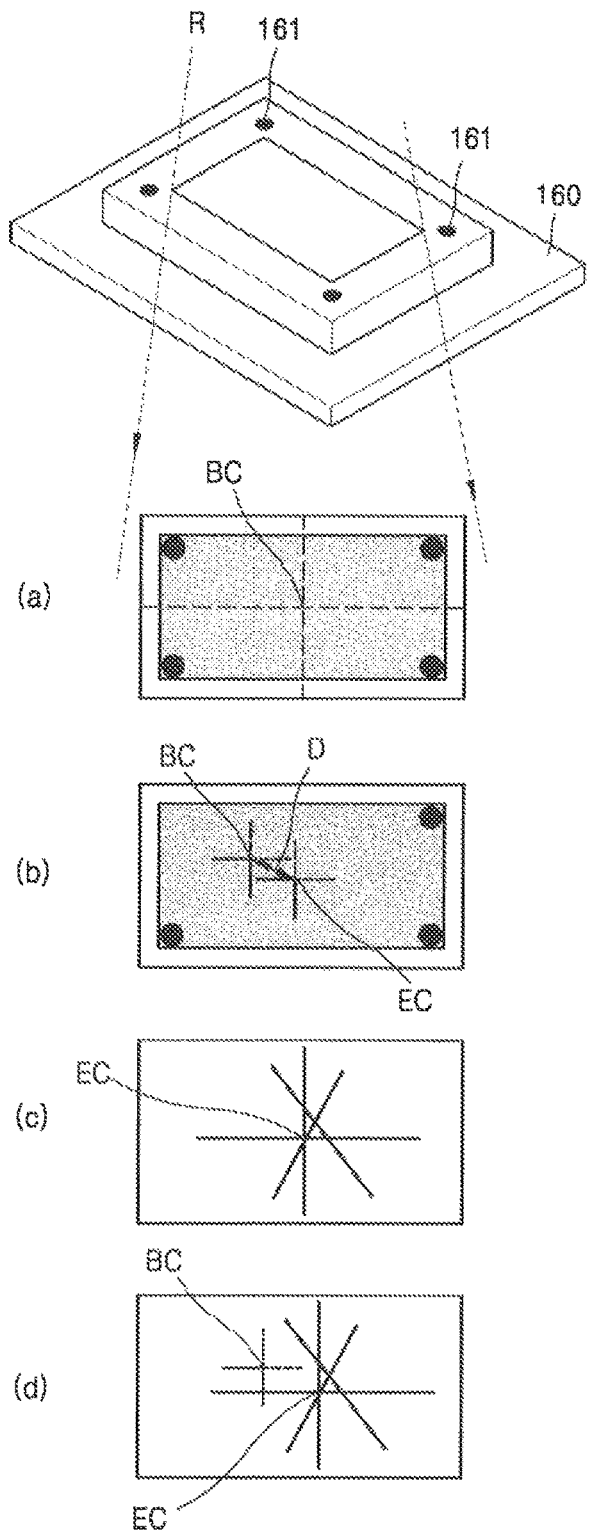

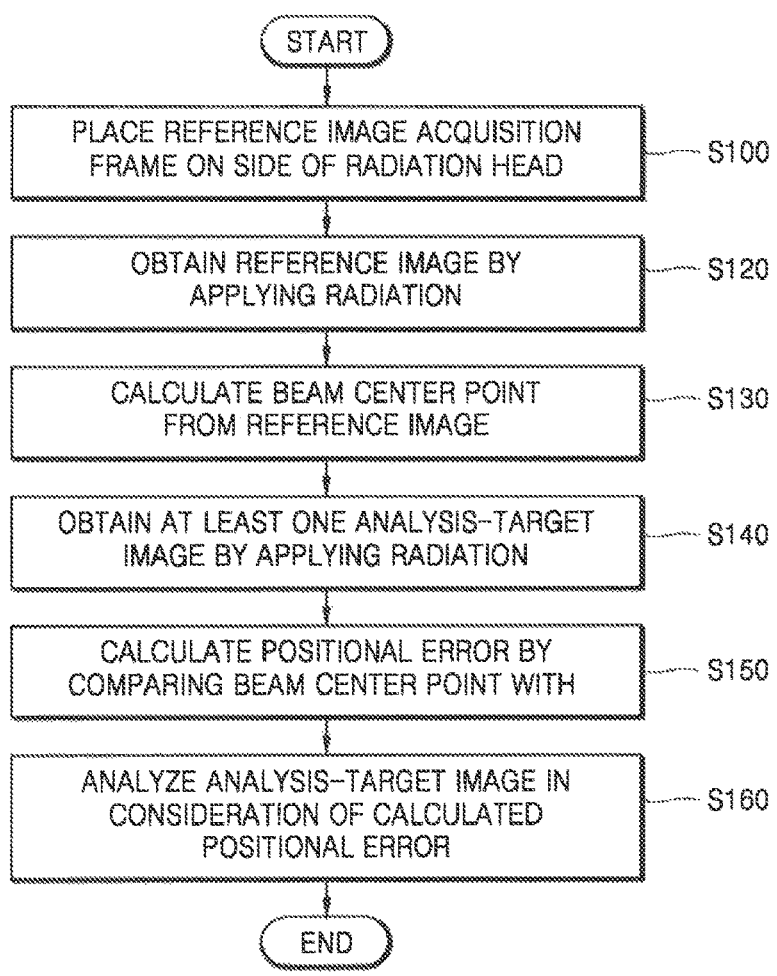

RADIATION THERAPY DEVICE AND QUALITY CONTROL METHOD FOR RADIATION THERAPY DEVICE

CROSS-REFERENCE TO RELATED APPLICATIONS

This application is the National Stage entry under 35 U.S.C. § 371 of International Application Number PCT/KR2015/007456 filed on Jul. 17, 2015, published on Jan. 21, 2016 under publication number WO 2016/010398 A1, which claims the benefit of priority under 35 U.S.C. § 119 of Korean patent application number 10-2014-0091325 filed Jul. 18, 2014.

TECHNICAL FIELD

Embodiments of the present invention relate to a radiation therapy device and a quality control method for the radiation therapy device, and more particularly, to a radiation therapy device including an image acquisition unit such as an electronic portal imaging device (EPID) and a quality control method for the radiation therapy device, the radiation therapy device and the quality control method being designed to calculate errors caused by variations in the position of the EPID and correct the errors.

BACKGROUND ART

Radiation therapy is a method of delaying or preventing the growth of malignant tissue or removing malignant tissue by damaging or destroying target tissue using high-energy waves such as X-rays or gamma rays, or high-energy particle rays such as electron rays or proton rays. Radiation therapy may be used to treat malignant tumors, medical diseases, and some skin diseases in addition to cancers. Radiosurgery using a large amount of radiation at one time instead of making an incision has recently been developed as a substitute for neurosurgery in which the cranium is cut.

Radiation therapy has become common, and about 60% or more of recent cancer patients receive radiation therapy. In addition to being used to treat tumors, radiation therapy may be used to treat large invasive tumors that are difficult to treat surgically or may be used, together with other surgical methods of treating an area of the body not removed by surgery, to reduce the size of tumors and make it easy to perform surgery, or may be used to destroy malignant cells remaining after surgery.

External radiation therapy devices configured to emit radiation from the outside of the body may be classified into low-energy X-ray therapy devices, radioisotope therapy devices, linear accelerators, particle accelerators, and so on, according to the methods of generating high-energy particles or radiation.

Although low-energy X-ray therapy devices had been used to treat skin diseases or deep parts of the body by using X-ray generators, the use of low-energy X-ray therapy devices is now rare.

Radioisotope therapy devices use gamma rays emitted from radioisotopes such as cobalt 60 (Co-60). Although radioisotope therapy devices use relatively high-energy gamma rays compared to low-energy X-ray therapy devices, the use of radioisotope therapy devices has been gradually reduced.

Linear accelerators, which are considered as standard radiation therapy devices, are capable of emitting X-ray beams and electron beams and transferring various forms of energy and have a high dose rate and a beam shape adjusting (beam-forming) function.

Particle accelerators, in which particles such as neutrons or protons are accelerated using a cyclotron accelerator, transferred through a beam transport tube, and ejected to a desired area through a nozzle, have a deeper Bragg peak than linear accelerators and are thus capable of concentrating energy only on a deep tumor while minimizing the dose in normal tissue.

In general, as the position of patients is intentionally changed or patients unconsciously move their bodies, the diagnosis accuracy or therapy effect of medical radiation devices decreases, and the dose of radiation absorbed in normal tissue around a lesion increases, thereby increasing the time and costs for treatment. Thus, medical radiation devices have been gradually advanced from a type in which a radiation head and a radiation detection unit face each other at fixed positions to a type in which a radiation head and a radiation detection unit are movable around a patient.

Recent medical radiation devices have been developed into a type in which a radiation head is attached to a gantry having an arm and a type using a ring-shaped gantry. Since a radiation source and a radiation detector are required to rotate around living body tissue in a state in which a radiation head and the radiation detector face each other with the living body, tissue being therebetween, a ring gantry structure or a C-arm gantry structure is mainly used.

The above-described background art is technical information that the inventors had or learned when or while inventing the present invention and may not be publicly known before the filing of the present patent application.

DETAILED DESCRIPTION OF THE INVENTION

Technical Problem

Objects of embodiments of the present invention are to provide a radiation therapy device including an image acquisition unit such as an electronic portal imaging device (EPID) and a quality control method for the radiation therapy device which are designed to calculate errors caused by variations in the position of the EPID and correct the errors.

Technical Solution

An embodiment of the present invention provides a radiation therapy device including: a main body; a gantry coupled to a side of the main part and rotatable relative to the main part in at least one direction; a radiation head provided on a side of the gantry to emit radiation; an image acquisition unit facing the radiation head to detect radiation emitted from the radiation head and obtain images by converting the detected radiation into electric signals; and a reference image acquisition frame provided on a side of the radiation head and including a plurality of markers formed thereon.

In the embodiment, the reference image acquisition frame may have a window shape in which an opening is formed, and the plurality of markers may be formed in an edge region of the reference image acquisition frame.

In the embodiment, a frame attachment guide may be formed on the side of the radiation head, and the reference image acquisition frame may be fixed to the frame attachment guide.

In the embodiment, the image acquisition unit is an electronic portal imaging device (EPID).

In the embodiment, the image acquisition unit may obtain a reference image in which the plurality of markers are included, and at least one analysis-target image, and the analysis-target image may be analyzed based on a beam center point calculated from the reference image.

In the embodiment, the image acquisition unit may calculate a positional error of the image acquisition unit by comparing the beam center point calculated from the reference image with a center point of the image acquisition unit, and may analyze the analysis-target image in consideration of the calculated positional error.

In the embodiment, the radiation therapy device may further include a positional error correcting unit configured to move the gantry, the radiation head, or the image acquisition unit in at least one direction.

Another embodiment of the present invention provides a quality control method for a radiation therapy device, the quality control method including: placing a reference image acquisition frame on a side of a radiation head, a plurality of markers being formed on the reference image acquisition frame; obtaining a reference image containing the plurality of markers by applying radiation from the radiation head; calculating a beam center point from the reference image; obtaining at least one analysis-target image by applying radiation from the radiation head; and analyzing the analysis-target image based on the beam center point calculated from the reference image.

In the embodiment, the analyzing of the analysis-target image based on the beam center point may include: calculating a positional error of the image acquisition unit by comparing the beam center point calculated from the reference image with a center point of the image acquisition unit; and analyzing the analysis-target image in consideration of the calculated positional error.

In the embodiment, the analyzing of the analysis-target image in consideration of the calculated positional error may be performed based on how much a center point of the analysis-target image is deviated from the beam center point (BC) calculated from the reference image.

In the embodiment, the obtaining of the reference image may be performed by emitting radiation in such a manner that all the plurality of markers are contained in the reference image.

In the embodiment, the reference image and the analysis-target image may be obtained using an EPID.

In the embodiment, the quality control method may further include correcting the positional error by moving the gantry, the radiation head, or the image acquisition unit in at least one direction.

Other aspects, features, and advantages will become apparent and more readily appreciated from the accompanying drawings, claims, and detailed description.

Advantageous Effects of the Invention

Embodiments of the present invention provide a radiation therapy device and a quality control method for the radiation therapy device which are designed to calculate errors caused by variations in the position of an electronic portal imaging device (EPID) and correct the errors.

In addition, quality control may be accurately/precisely performed using the EPID, and the use of digital images may improve accuracy.

Furthermore, radiation films used in the related art may not be used owing to the use of the EPID, and thus costs incurred by the use of radiation films may be saved.

In addition, the use of the EPID enables automatic quality control and may reduce time, costs, and manpower necessary for quality control.

DESCRIPTION OF THE DRAWINGS

FIG. 4 is a view illustrating quality control procedures using the radiation therapy device illustrated in FIG. 1.

FIG. 5 is a flowchart illustrating a quality control method for the radiation therapy device according to an embodiment of the present invention.

BEST MODE

Figure 1:
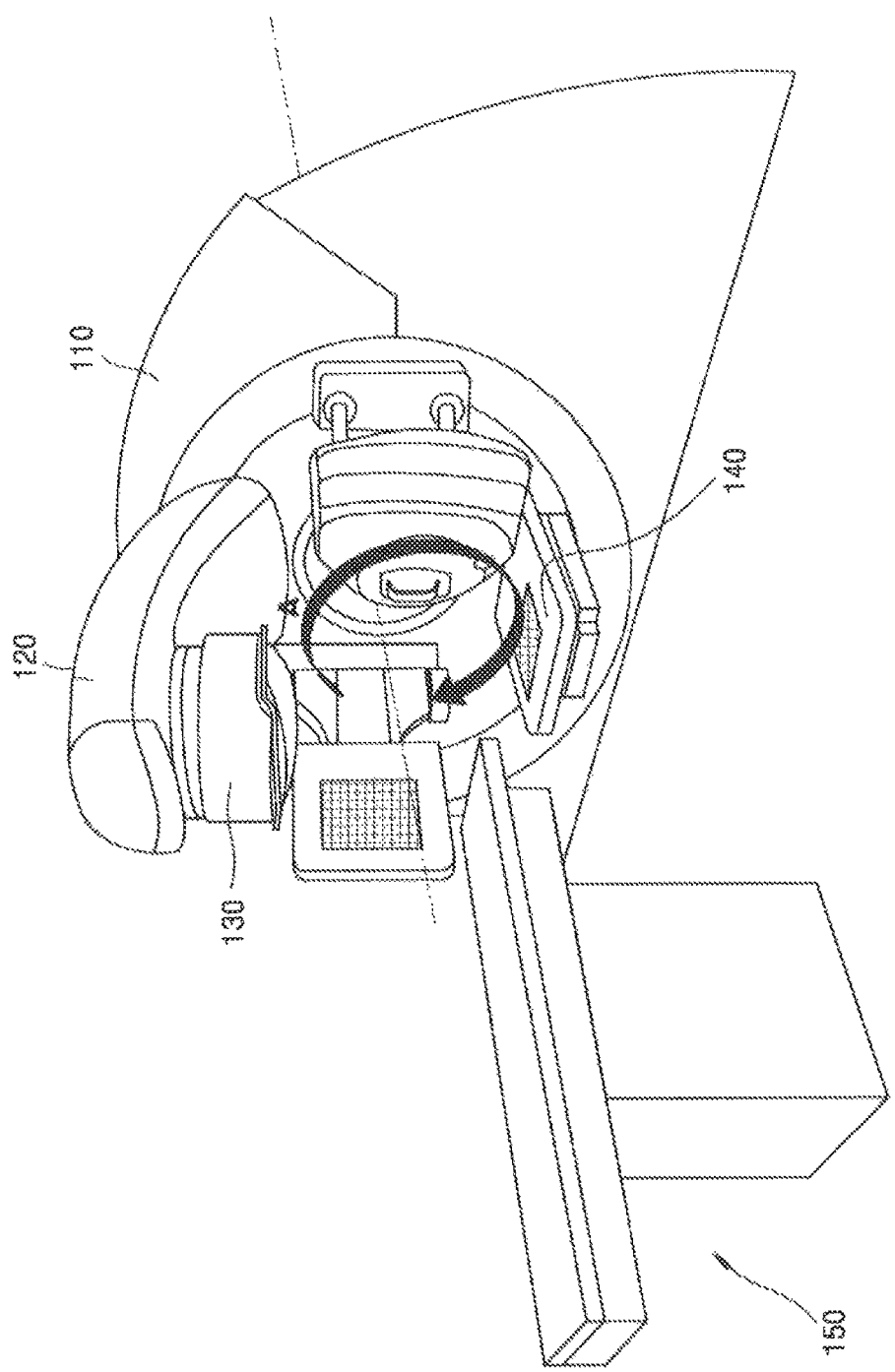
FIG. 1 is a view illustrating a radiation therapy device according to an embodiment of the present invention.

The present invention may be variously modified, and various embodiments may be provided according to the present invention. Hereinafter, some embodiments will be illustrated in the accompanying drawings and described in detail. Effects and features of the present invention, and implementation methods thereof will be clarified through the following embodiments described with reference to the accompanying drawings. However, the present invention is not limited to the following embodiments but may be implemented in various forms. In the following embodiments, it will be understood that although the terms "first", "second", etc. are used to describe various elements, these elements should not be limited by these terms. These elements are only used to distinguish one element from another. The terms of a singular form may include plural forms unless referred to the contrary. In addition, terms such as "include" or "comprise" specify features or the presence of stated elements, but do not exclude other features or elements. In the drawings, the sizes of elements may be exaggerated for clarity. For example, in the drawings, the size or thickness of each element may be arbitrarily shown for illustrative purpose, and thus the present invention should not be construed as being limited thereto.

Hereinafter, the embodiments of the present invention will be described in detail with reference to the accompanying drawings. In the following description given with reference to the accompanying drawings, the same elements or corresponding elements are denoted with the same reference numeral, and overlapping descriptions thereof will be omitted.

Figure 2:
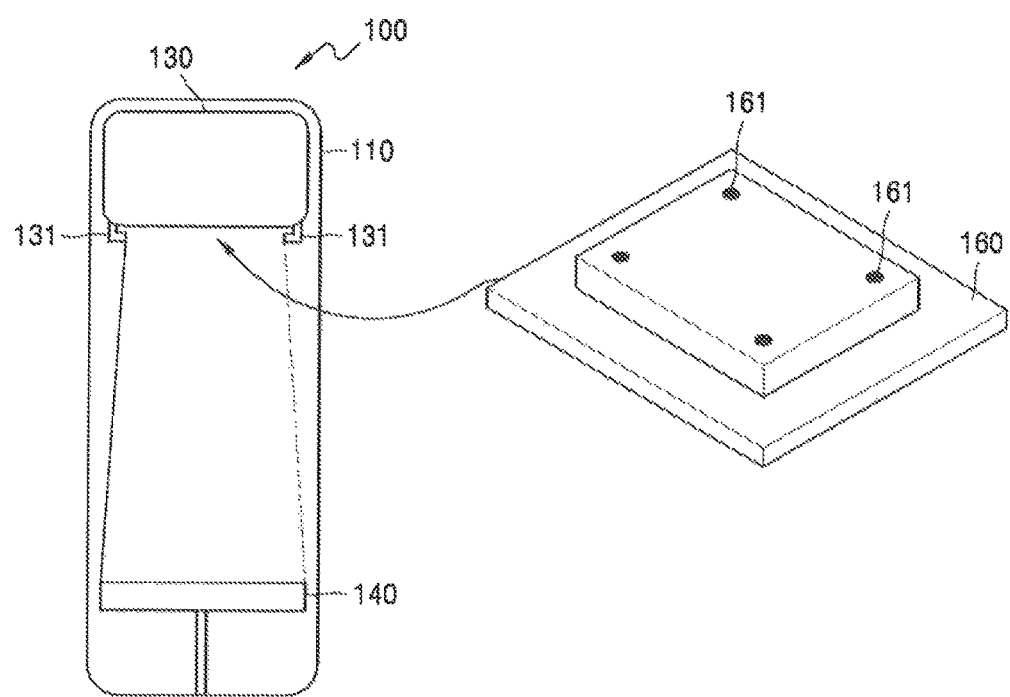
FIGS. 2 and 3 are schematic views illustrating the radiation therapy device illustrated in FIG. 1.

FIG. 1 is a view illustrating a radiation therapy device 100 according to an embodiment of the present invention, and FIG. 2 is a schematic view illustrating the radiation therapy device 100 illustrated in FIG. 1.

Referring to FIGS. 1 and 2, according to the embodiment of the present invention, the radiation therapy device 100 includes a main part 110, a gantry 120, a radiation head 130, an image acquisition unit 140, a bed part 150, and a reference image acquisition frame 160. This will now be described in more detail.

Radiation therapy is a cancer treatment method in which radiation is concentrated on a tumor to result in a high radiation dose. A treatment technique for concentrating radiation on a tumor while minimally damaging surrounding normal organs, a precise radiation therapy device, and various imaging devices for monitoring are definitely required for success in radiation therapy.

Along with the recent increase in the use of high-precision radiation therapy devices, high-dose treatment using advanced techniques has widespread. Although the efficiency of removing tumors can be increased by high doses of radiation, high-dose radiation also increases the possibility of radiation accidents caused by erroneous application of radiation. Thus, treatment or therapy devices are required by law to provide strict quality assurance so as to prevent such accidents.

Electronic portal imaging devices (EPIDs) have been mainly used to check the position of patients to accurately perform treatment, and attempts to use EPIDs as means for assuring the quality, of radiation therapy devices have recently increased. Although the use of EPIDs for quality assurance is advantageous in terms of ease and efficiency, the position reproducibility of EPIDs may not be constant between measurements, and the position of EPIDs may be varied by gravity when gantries of radiation therapy devices are rotated. Therefore, quality assurance and image analysis using EPID images have many difficulties and limitations. Due to these reasons, quality assurance using EPIDs requires systems for removing positional errors and improving the positional accuracy of EPIDs by correcting images captured at various gantry angles.

According to the embodiment of the present invention, the radiation therapy device 100 captures a reference image using the reference image acquisition frame 160 provided on a side of the gantry 120 and analyzes images using the reference image so as to calculate and correct measurement errors caused by variations in the position of the image acquisition unit 140 such as an EPID. This will now be described in more detail.

Referring again to FIGS. 1 and 2, the main part 110 forms a base part of the radiation therapy device 100 and functions as a reference for rotation of the gantry 120, the radiation head 130, and the image acquisition unit 140.

The gantry 120 is coupled to a side of the main part 110 and is rotatable in at least one direction relative to the main part 110. In this case, the image acquisition unit 140 facing the radiation head 130 of the gantry 120 may be rotated together with the gantry 120. That is, the gantry 120, the radiation head 130, and the image acquisition unit 140 may be rotated in a direction indicated by an arrow A in FIG. 1 (or in an opposite direction).

The radiation head 130 configured to emit radiation is provided on a side of the gantry 120. The radiation head 130 may emit X-rays, gamma rays, high-energy electrons, high-energy protons, or other high-energy particles.

In addition, the radiation head 130 may include one of an X-ray generator, a radioisotope source, and a linear accelerator. Alternatively, the radiation head 130 may receive a beam of high-energy particles which are accelerated by a particle accelerator installed outside the radiation therapy device 100 and may emit the high-energy particle beam. Alternatively, the radiation head 130 may be implemented as a multi-leaf collimator (MLC). If the radiation head 130 is implemented as an MLC, beam forming is possible inside the radiation head 130, and thus radiation energy may be more efficiently transferred.

A frame attachment guide 131 may protrude in a direction in which the radiation head 130 emits radiation, and the reference image acquisition frame 160 may be coupled to the frame attachment guide 131.

The image acquisition unit 140 is an image sensor for obtaining images by detecting radiation and converting the radiation into electric signals. In some embodiments, an EPID may be used as the image acquisition unit 140. In detail, EPID technology is used in high-energy radiation therapy to obtain images by detecting radiation passing through a patient and converting the detected radiation into electric signals, so as to check the location of a diseased part. The image acquisition unit 140 may be used to obtain a reference image and analysis target images as described later.

The bed part 150 on which a patient can lie may be configured to move in x-axis, y-axis, and z-axis directions relative to radiation emitted from the radiation head 130.

The reference image acquisition frame 160 may have a window shape in which an opening is formed, and a plurality of markers 161 may be formed on corner portions of the reference image acquisition frame 160. In a state in which the reference image acquisition flame 160 is inserted in the frame attachment guide 131 of the radiation head 130, the reference image acquisition frame 160 may be fixed to the radiation head 130.

According to the embodiment of the present invention, the radiation therapy device 100 may further include a positional error correcting unit (not shown). The positional error correcting unit (not shown) may include a motor and an actuator and may be installed on at least one of the gantry 120, the radiation head 130, or the image acquisition unit 140 in a movable manner in an x-axis, y-axis, or z-axis direction of the gantry 120, the radiation head 130, or the image acquisition unit 140. Owing to the positional error correcting unit (not shown) configured to correct positional errors, the quality of the radiation therapy device may be controlled.

FIG. 4 is a view illustrating quality control procedures using the radiation therapy device illustrated in FIG. 1.

As illustrated in FIG. 4(a), in a state in which the reference image acquisition frame 160 having the markers 161 is placed on a side of the radiation head 130, the radiation head 130 emits radiation R, and a reference image including the markers 161 is obtained.

At this time, the radiation R may be emitted from the radiation head 130 to a sufficiently large area, and thus the reference image may include ail the markers 161 formed in a edge region of the reference image acquisition frame 160.

Then, a beam center point BC is calculated from the reference image obtained as described above. For example, the beam center point BC may be calculated based on a cross point between diagonal lines passing through four markers appearing in the reference image or a center point of the length and width of a rectangle formed by the four markers in the reference image, or any other method may be used to calculate the beam center point BC.

Figure 3:
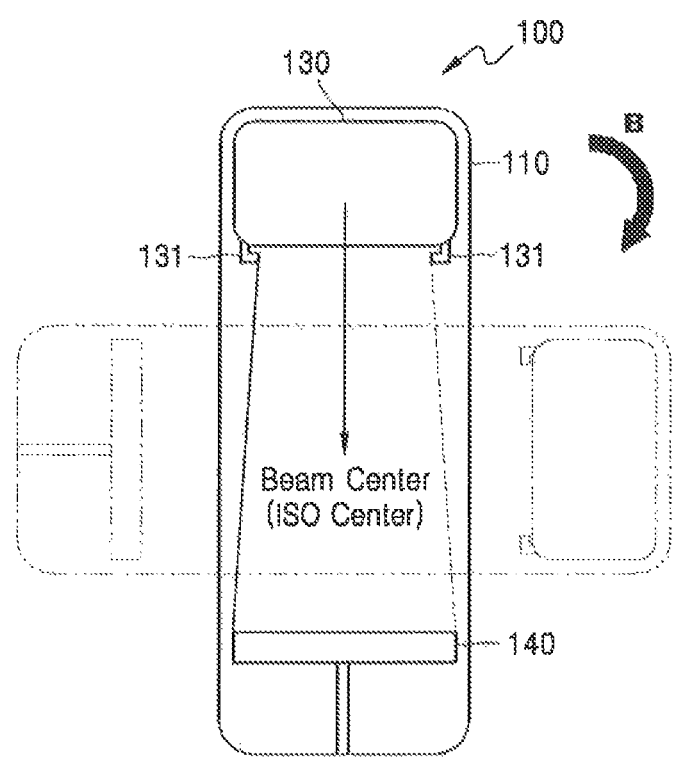

In this state, the gantry 120, the radiation head 130, and the image acquisition unit 140 may be rotated relative to the main part 110 by a predetermined angle. In this case, the position of the image acquisition unit 140 may be varied because of factors such as the weight of the image acquisition unit 140. That is, as illustrated in FIG. 3, when the gantry 120, the radiation head 130, and the image acquisition unit 140 are rotated in a direction of an arrow B with respect to the main part 110, the position of the image acquisition unit 140 may be varied because of the weight of the image acquisition unit 140. Therefore, as illustrated in FIG. 4B, there may be an error D between a center point EC of the image acquisition unit 140 and the beam center point BC calculated from the reference image.

In a state in which the position of the image acquisition unit 140 is deviated to some degree as described above, the radiation head 130 may emit radiation at different angles, and one or more analysis-target images may be obtained as illustrated in FIG. 4C. For example, an analysis-target image may be obtained each time the radiation head 130 is rotated 45°. In this case, eight analysis-target images may be obtained in total.

At this time, since there is a certain amount of deviation in the position of the image acquisition unit 140, if quality control is performed based on the center point EC of the image acquisition unit 140, positional errors may be inevitably generated, and thus precise quality control may not be performed. Therefore, as illustrated in FIG. 4D, according to the embodiment of the present invention, quality control is performed by analyzing the analysis-target images based on the beam center point BC calculated from the reference image instead of the center point EC of the image acquisition unit 140, thereby improving the accuracy and reliability of the quality control.

In an example of quality control, center points of beam regions of the above-mentioned eight analysis-target images may be calculated, and deviations of the center points from the beam center point BC calculated from the reference image may be inspected. That is, if the center points of the analysis-target images deviate from the beam center point BC calculated from the reference image by a predetermined distance (for example, 1 mm) or less, it may be determined that quality control is satisfactory. However, if the center points of the analysis-target images deviate from the beam center point BC calculated from the reference image by a distance greater than the predetermined distance, it may be determined that quality control is not satisfactory, and the radiation therapy device 100 may be adjusted. As described above, since quality control is performed by analyzing the analysis-target images based on the beam center point BC calculated from the reference image instead of the center point EC of the image acquisition unit 140, the accuracy and reliability of the quality control may be improved.

In addition, the gantry 120, the radiation head 130, or the image acquisition unit 110 may be moved in an x-axis, y-axis, or z-axis direction using the positional error correcting unit (not shown) installed on at least one of the gantry 120, the radiation head 130, or the image acquisition unit 140, so as to correct positional errors for quality control of the radiation therapy device 100.

As described above, according to the embodiments of the present invention, errors caused by variations in the position of the EPID of the radiation therapy device may be calculated and corrected. In addition, quality control may be accurately/precisely performed using the EPID, and the use of digital images may improve accuracy. Furthermore, radiation films used in the related art may not be used owing to the use of the EPID, and thus costs incurred by the use of radiation films may be saved. In addition, the use of the EPID may enable automatic quality control and may reduce time, costs, and manpower necessary for quality control.

MODE OF THE INVENTION

Hereinafter, a quality control method for the radiation therapy device will be described according to an embodiment of the present invention.

FIG. 5 is a flowchart illustrating a quality control method for the radiation therapy device according to an embodiment of the present invention. Referring to FIG. 5, the quality control method includes: placing the reference image acquisition frame having the plurality of markers on a side of the radiation head (operation S110); obtaining a reference image including the plurality of markers by applying radiation from the radiation head (operation S120); calculating a beam center point from the reference image (operation S130); obtaining one or more analysis-target images by applying radiation from the radiation head (operation S140); calculating a positional error of the image acquisition unit by comparing the beam center point calculated from the reference image with a center point of the EPID (operation S150); and analyzing the analysis-target images in consideration of the calculated positional error (operation S160).

First, the reference image acquisition frame including the plurality of markers is placed on a side of the radiation head (operation S110). In detail, the reference image acquisition frame 160 may have a window shape in which an opening is formed, and the plurality of markers 161 may be formed at corner portions of the reference image acquisition frame 160. In a state in which the reference image acquisition frame 160 is inserted in the frame attachment guide 131 of the radiation head 130, the reference image acquisition frame 160 may be fixed to the radiation head 130.

Next, a reference image including the plurality of markers is obtained by applying radiation from the radiation head (operation S120). That is, in a state in which the reference image acquisition frame 160 having the markers 161 is placed on the side of the radiation head 130, the radiation head 130 emits radiation R, and a reference image including the plurality of markers 161 is obtained. At this time, the radiation R may be emitted from the radiation head 130 to a sufficiently large area, and thus the reference image may include all the markers 161 formed in an edge region of the reference image acquisition frame 160.

Next, a beam center point is calculated from the reference image (operation S130). For example, the beam center point BC may be calculated based on a cross point between diagonal lines passing through four markers appearing in the reference image or a center point of the length and width of a rectangle formed by the four markers, or any other method may be used to calculate the beam center point BC.

Next, one or more one analysis-target images are obtained by applying radiation from the radiation head (operation S140). For example, an analysis-target image may be obtained each time the radiation head 130 is rotated 45°. In this case, eight analysis-target images may be obtained in total.

Next, a positional error of the image acquisition unit is calculated by comparing the beam center point calculated from the reference image with the center point of the EPID (operation S150), and the analysis-target images are analyzed in consideration of the calculated positional error (operation S160).

For example, center points of beam regions of the above-mentioned eight analysis-target images may be calculated, and deviations of the center points from the beam center point BC calculated from the reference image may be inspected. That is, if the center points of the analysis-target images deviate from the beam center point BC calculated from the reference image by a predetermined distance (for example, 1 mm) or less, it may be determined that quality control is satisfactory. However, if the center points of the analysis-target images deviate from the beam center point BC of the reference image by a distance greater than the predetermined distance, it may be determined that quality control is not satisfactory, and the radiation therapy device 100 may be adjusted. As described above, since quality control is performed by analyzing the analysis-target images based on the beam center point BC calculated from the reference image instead of the center point EC of the image acquisition unit 140, the accuracy and reliability of the quality control may be improved.

Although not shown in the drawing, the quality control method may further include correcting a positional error of at least one of the gantry 120. the radiation head 130, or the image acquisition unit 140. That is, the gantry 120, the radiation head 130, or the image acquisition unit 140 may be moved in an x-axis, y-axis, or z-axis direction using the positional error correcting unit (not shown) installed on at least one of the gantry 120, the radiation head 130, or the image acquisition unit 140, so as to correct positional errors for quality control of the radiation therapy device.

As described above, according to the embodiments of the present invention, errors caused by positional variations of the EPID of the radiation therapy device may be calculated and corrected. In addition, quality control may be accurately/precisely performed using the EPID, and the use of digital images may improve accuracy. Furthermore, radiation films used in the related art may not be used owing to the use of the EPID, and thus costs incurred by the use of radiation films may be saved. In addition, the use of the EPID may enable automatic quality control and may reduce time, costs, and manpower necessary for quality control.

While the present invention has been described with reference to the accompanying drawings according to embodiments, these embodiments are for illustrative purposes only, and it will be understood by those of ordinary skill in the art that various changes and modifications may be made therefrom. Therefore, the scope and spirit of the present invention should be defined by the following claims.

INDUSTRIAL APPLICABILITY

Embodiments of the present invention may be applied to radiation therapy devices and quality control methods for radiation therapy devices.

The invention claimed is:

1. A radiation therapy device comprising: a main part; a gantry coupled to a side of the main part and rotatable relative to the main part in at least one direction; a radiation head provided on a side of the gantry to emit radiation; an image acquisition unit facing the radiation head to detect radiation emitted from the radiation head and obtain images by converting the detected radiation into electric signals; a reference image acquisition frame provided on a side of the radiation head and comprising a plurality of markers formed thereon; and a positional error correcting unit configured to move the gantry, the radiation head, or the image acquisition unit in at least one direction so as to correspond a positional error of the image acquisition unit, wherein the image acquisition unit obtains a reference image in which the plurality of markers are included, and at least one analysis-target image, wherein the positional error of the image acquisition unit is calculated by comparing the beam center point calculated from the reference image with a center point of the image acquisition unit, and wherein the analysis-target image is analyzed based on a beam center point calculated from the reference image in consideration of the calculated positional error.

2. The radiation therapy device of claim 1, wherein the reference image acquisition frame has a window shape in which an opening is formed, and the plurality of markers are formed in an edge region of the reference image acquisition frame.

3. The radiation therapy device of claim 1, wherein a frame attachment guide is formed on the side of the radiation head, and the reference image acquisition frame is fixed to the frame attachment guide.

4. The radiation therapy device 1, wherein the image acquisition unit is an electronic portal imaging device (EPID).

5. A quality control method for a radiation therapy device, the quality control method comprising:
placing a reference image acquisition frame on a side of a radiation head, a plurality of markers being formed on the reference image acquisition frame;
obtaining a reference image containing the plurality of markers by applying radiation from the radiation head;
calculating a beam center point from the reference image;
obtaining at least one analysis-target image by applying radiation from the radiation head;
analyzing the analysis-target image based on the beam center point calculated from the reference image; and
correcting the positional error by moving the gantry, the radiation head, or the image acquisition unit in at least one direction,
wherein the analyzing of the analysis-target image based on the beam center point comprises:
calculating a positional error of the image acquisition unit by comparing the beam center point calculated from the reference image with a center point of the image acquisition unit; and
analyzing the analysis-target image in consideration of the calculated positional error.

6. The quality control method of claim 5, wherein the analyzing of the analysis-target image in consideration of the calculated positional error is performed based on how much a center point of the analysis-target image is deviated from the beam center point (BC) calculated from the reference image.

7. The quality control method of claim 5, wherein the obtaining of the reference image is performed by emitting radiation in such a manner that all the plurality of markers are contained in the reference image.

8. The quality control method of claim 5, wherein the reference image and the analysis-target image are obtained using an EPID.

* * * * *